United States Patent
Lambert

(10) Patent No.: US 9,901,552 B2
(45) Date of Patent: *Feb. 27, 2018

(54) COMPOSITIONS AND METHODS FOR TRANSDERMAL DELIVERY OF AMPHETAMINE

(71) Applicant: NOVEN PHARMACEUTICALS, INC., Miami, FL (US)

(72) Inventor: Robert L. Lambert, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/285,174

(22) Filed: Oct. 4, 2016

(65) Prior Publication Data

US 2017/0246126 A1    Aug. 31, 2017

Related U.S. Application Data

(63) Continuation of application No. 14/062,360, filed on Oct. 24, 2013, now Pat. No. 9,474,722.

(60) Provisional application No. 61/718,537, filed on Oct. 25, 2012, provisional application No. 61/791,018, filed on Mar. 15, 2013.

(51) Int. Cl.
| | | |
|---|---|---|
| *A61K 31/137* | (2006.01) | |
| *A61K 9/70* | (2006.01) | |
| *A61K 47/34* | (2017.01) | |
| *A61K 47/32* | (2006.01) | |

(52) U.S. Cl.
CPC .......... *A61K 31/137* (2013.01); *A61K 9/7084* (2013.01); *A61K 47/32* (2013.01); *A61K 47/34* (2013.01)

(58) Field of Classification Search
None
See application file for complete search history.

(56) References Cited

U.S. PATENT DOCUMENTS

| | | |
|---|---|---|
| 4,994,278 A | 2/1991 | Sablotsky et al. |
| 8,591,941 B2 | 11/2013 | Kanios et al. |
| 8,703,175 B2 | 4/2014 | Kanios et al. |
| 9,456,993 B2 | 10/2016 | Lambert |
| 9,474,722 B2 | 10/2016 | Lambert |
| 2002/0115725 A1 | 8/2002 | Epstein et al. |
| 2003/0170195 A1 | 9/2003 | Houze et al. |
| 2005/0048104 A1 | 3/2005 | Venkatraman |
| 2006/0078604 A1 | 4/2006 | Kanios et al. |
| 2006/0078640 A1 | 4/2006 | Okutsu et al. |
| 2008/0220054 A1 | 9/2008 | Shastri et al. |
| 2011/0097384 A1 | 4/2011 | Kanios et al. |
| 2013/0015092 A1 | 1/2013 | Suzuki et al. |
| 2014/0243764 A1 | 8/2014 | Kanios et al. |
| 2014/0271865 A1 | 9/2014 | Lambert et al. |
| 2014/0276478 A1 | 9/2014 | Liao et al. |

FOREIGN PATENT DOCUMENTS

WO    WO 2011/042913 A2    4/2011

OTHER PUBLICATIONS

International Search Report dated Dec. 13, 2013 in application No. PCT/US2013/0666523.
Office Action dated Jul. 30, 2015 in U.S. Appl. No. 14/585,964 (now U.S. Pat. No. 9,456,993).
Office Action dated Oct. 8, 2015 in U.S. Appl. No. 14/585,964 (now U.S. Pat. No. 9,456,993).
Office Action dated Oct. 16, 2015 in U.S. Appl. No. 14/585,964 (now U.S. Pat. No. 9,456,993).
Notice of Allowance dated Jun. 6, 2016 in U.S. Appl. No. 14/585,964 (now U.S. Pat. No. 9,456,993).
International Search Report dated Mar. 13, 2015 in application No. PCT/US2014/071406.
Office Action dated Jul. 17, 2015 in U.S. Appl. No. 14/062,360 (now U.S. Pat. No. 9,474,722).
Office Action dated Jan. 20, 2016 in U.S. Appl. No. 14/062,360 (now U.S. Pat. No. 9,474,722).
Notice of Allowance dated Jun. 24, 2016 in U.S. Appl. No. 14/062,360 (now U.S. Pat. No. 9,474,722).

*Primary Examiner* — Robert A Wax
*Assistant Examiner* — Danah Al-Awadi
(74) *Attorney, Agent, or Firm* — Foley & Lardner LLP

(57) ABSTRACT

Compositions for the transdermal delivery of amphetamine in a flexible, finite form are described. The compositions comprise a polymer matrix that includes amphetamine or a pharmaceutically acceptable salt or prodrug thereof and a backing layer comprising a polyurethane film layer and a polyester film layer, with a polyurethane adhesive disposed therebetween. Related methods also are described. Also described are compositions that exhibit a short onset period and a long duration of therapeutic effect

20 Claims, 2 Drawing Sheets

COMPOSITIONS AND METHODS FOR TRANSDERMAL DELIVERY OF AMPHETAMINE

This application is a continuation of U.S. patent application Ser. No. 14/062,360, filed Oct. 24, 2013, now issued as U.S. Pat. No. 9,474,722, which claims the priority benefits of U.S. Provisional patent application Nos. 61/718,537, filed Oct. 25, 2012, and 61/719,018, filed Mar. 15, 2013, the entire contents of which are incorporated herein by reference.

BACKGROUND

The present invention relates generally to the transdermal delivery of amphetamine, and to methods of transdermally delivering amphetamine, such as may be desired for achieving central nervous system stimulation, such as for the treatment of attention deficit disorder (ADD), attention deficit hyperactivity disorder (ADHD), or for the treatment of narcolepsy.

Many factors influence the design and performance of transdermal drug delivery compositions. These include the individual drugs themselves, the physical and chemical characteristics of the compositions' components and their performance and behavior relative to other components, external and environmental conditions during manufacturing and storage, properties of the application site, the desired rate of drug delivery and therapeutic onset, the desired drug delivery profile, and the intended duration of delivery, among others.

Compositions for the transdermal delivery of amphetamine are known, but there remains a need for compositions that exhibit suitable physical and pharmacokinetic properties.

SUMMARY OF THE INVENTION

Described herein are compositions for the transdermal delivery of amphetamine in the form of a flexible finite system for topical application, comprising (i) a polymer matrix comprising amphetamine or a pharmaceutically acceptable salt or prodrug thereof and (ii) a backing layer comprising (a) a polyurethane film layer and (b) a polyester film layer, wherein an adhesive is disposed between the polyurethane film layer and the polyester film layer, wherein the polyurethane film layer of the backing layer is adjacent the polymer matrix. In some embodiments, the polyurethane film layer is comprised of a polyether aromatic polyurethane polymer. In some embodiments, the polyurethane film layer has a thickness of about 1.5 mils. In some embodiments, the polyester film layer has a thickness of from about 0.4 mils to 0.6 mils. In some embodiments, the adhesive is a polyurethane adhesive.

In accordance with any of the embodiments, the adhesive of the backing layer may be a polyurethane adhesive, such as an isocyanate-terminated polyether urethane or an isocyanate-terminated polyester urethane, and optionally may be a cured adhesive, such as a cured isocyanate-terminated polyether urethane or a cured isocyanate-terminated polyester urethane, such as an adhesive cured by moisture or a curing agent, such as an epoxy curing agent. Additionally or alternatively, in accordance with any embodiments, the adhesive may be a two-component adhesive, such as an adhesive comprising a polyurethane adhesive and a coreactant.

In accordance with any of the embodiments, the amphetamine may be d-amphetamine free base. In accordance with any of the embodiments, the polymer matrix may comprise at least one acrylic polymer, including at least one non acid-functional acrylic polymer, such as a non acid-functional acrylic polymer that includes methacrylate (or methyl acrylate) and 2-ethylhexyl acrylate monomers and/or methacrylate (methyl acrylate), 2-ethylhexyl acrylate, and amide group-containing monomers, and optionally butyl acrylate monomers, and/or methyl methacrylate monomers. In accordance with any of the embodiments, the polymer matrix comprises about 10-20% by weight amphetamine or a pharmaceutically acceptable salt or prodrug thereof. In accordance with some embodiments, the polymer matrix comprises (a) a first non acid-functional acrylic polymer that includes 50% methacrylate (methyl acrylate) monomers and 50% 2-ethylhexyl acrylate monomers, based on the weight of the first acrylic polymer; (b) a second non acid-functional acrylic polymer that includes methacrylate monomers (methyl acrylate), 2-ethylhexyl acrylate monomers, and amide group-containing monomers, and optionally butyl acrylate monomers, and (c) about 10-20% by weight amphetamine or a pharmaceutically acceptable salt or prodrug thereof such as comprising 67.5% by weight of the first non acid-functional acrylic polymer, 17.5% by weight of the second non acid-functional acrylic polymer, and 15% by weight amphetamine, based on the total dry weight of the polymer matrix.

In accordance with any of the embodiments, the polymer matrix may have a coat weight of about 6-8 mg/cm$^2$, based on the active surface area of the polymer matrix. In accordance with any of the embodiments, the composition may comprise about 1 mg/cm$^2$ amphetamine. In accordance with any of the embodiments, the flexible, finite system may have a size of from about 2 cm$^2$ to about 60 cm$^2$, or of from about 5 cm$^2$ to about 30 cm$^2$. In accordance with any of the embodiments, the composition may further comprise a release liner.

In accordance with any of the embodiments, the composition may deliver amphetamine over a period of time of about 8-10 hours. In accordance with any of the embodiments, the composition may exhibit an onset period of from about 30 minutes to about 90 minutes. In accordance with any of the embodiments, composition may exhibit a duration of therapeutic effect of at least about 12 hours from the time of application of the composition, when it is removed at about 9 hours after application. In accordance with any of the embodiments, the composition may exhibit a drug depletion of at least about 85% to about 93% at about 8 to 10 hours after application.

Also described are methods for the transdermal delivery of amphetamine, comprising topically applying any composition as described herein to the skin or mucosa of a subject in need thereof. In accordance with any of the embodiments, the onset period may be from about 30 minutes to about 90 minutes. In accordance with any of the embodiments, the duration of therapeutic effect may be at least about 12 hours from the time of application of the composition, when it is removed at about 9 hours after application. In accordance with any of the embodiments, the composition may exhibit a drug depletion of at least about 85% to about 93% at about 8 to 10 hours after application.

Also described are compositions for the transdermal delivery of amphetamine in the form of a flexible finite system for topical application, wherein the composition exhibits one or more of: (a) an onset period of about 30 minutes to about 90 minutes; (b) a duration of therapeutic effect of at least about 12 hours; and/or (c) a drug depletion such that at least about 85% to about 93% of the drug formulated in the compositions is delivered or depleted from the composition at about 8-10 hours after application.

DETAILED DESCRIPTION

Figure 1A:
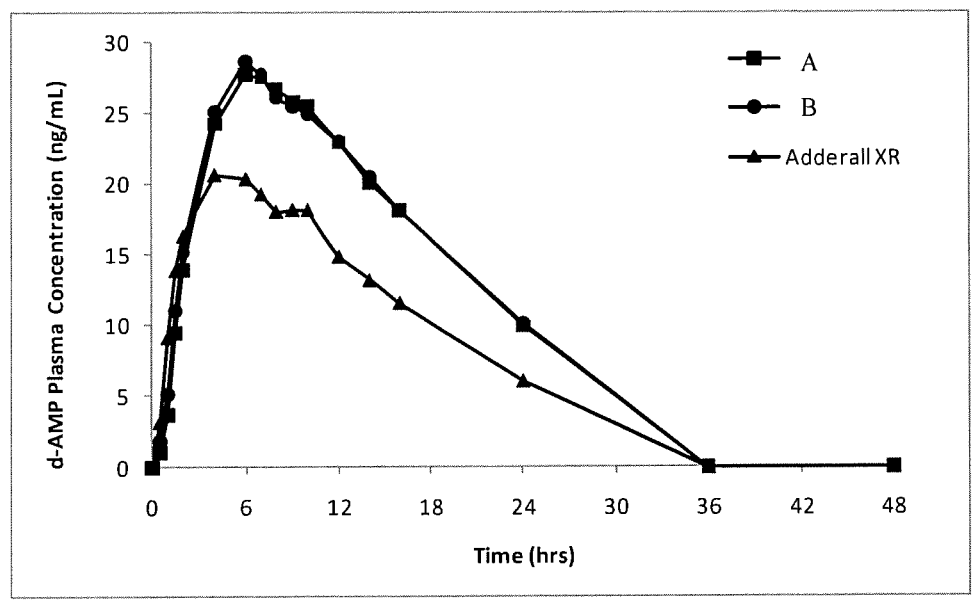
FIG. 1A shows plasma levels of d-amphetamine (mg/ml) over 48 hours after Treatment A (♦), Treatment B (■) or Treatment C (▲) of Example 4 below.

Described herein are compositions and methods for the transdermal delivery of amphetamine in a flexible, finite form (e.g., "patch"-type systems). The compositions in flexible, finite form comprise a polymer matrix that includes amphetamine or a pharmaceutically acceptable salt thereof and a backing layer. The compositions exhibit satisfactory physical properties while also achieving satisfactory pharmacokinetic profiles.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein means that the described composition (e.g., polymer matrix, etc.) comprises less than about 5%, less than about 3%, or less than about 1% by weight, based on the total weight of the composition at issue, of the excluded component(s).

As used herein "subject" denotes any mammal in need of drug therapy, including humans. For example, a subject may be suffering from or at risk of developing a condition that can be treated or prevented with amphetamine (such as ADD or narcolepsy), or may be taking amphetamine for other purposes.

As used herein, the terms "topical" and "topically" mean application to a skin or mucosal surface of a mammal, while the terms "transdermal" and "transdermal" connote passage through the skin or mucosa (including oral, buccal, nasal, rectal and vaginal mucosa), into systemic circulation. Thus, the compositions described herein may be applied topically to a subject to achieve transdermal delivery of amphetamine.

As used herein, the phrases "therapeutically effective amount" and "therapeutic level" mean that drug dosage or plasma concentration in a subject, respectively, that provides the specific pharmacological effect for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As used herein, "active surface area" means the surface area of the drug-containing polymer matrix of the transdermal drug delivery system.

The compositions described herein are in a "flexible, finite form." As used herein, the phrase "flexible, finite form" means a substantially solid form capable of conforming to a surface with which it comes into contact, and capable of maintaining contact so as to facilitate topical application. Such systems in general are known in the art and commercially available, such as transdermal drug delivery patches.

The compositions comprise a drug-containing polymer matrix that releases amphetamine upon application to the skin (or any other surface noted above). The compositions in flexible, finite form also include a backing layer in addition to the drug-containing polymer matrix layer. In some embodiments, the compositions in flexible, finite form may include a release liner layer in addition to a drug-containing polymer matrix layer and backing layer.

As used herein, "drug-containing polymer matrix" refers to a polymer composition which contains one or more drugs, such as amphetamine, and a polymer, such as a pressure-sensitive adhesive polymer or a bioadhesive polymer. A polymer is an "adhesive" or "bioadhesive" if it has the properties of adhesiveness per se. Other polymers can function as an adhesive or bioadhesive by the addition of tackifiers, plasticizers, crosslinking agents or other excipients. Thus, in some embodiments, the polymer optionally comprises tackifiers, plasticizers, crosslinking agents or other additives known in the art.

As used herein, the term "pressure-sensitive adhesive" refers to a viscoelastic material which adheres instantaneously to most substrates with the application of very slight pressure and remains permanently tacky. As noted above, a polymer is a pressure-sensitive adhesive polymer if it has the properties of a pressure-sensitive adhesive per se. Other polymers may function as a pressure-sensitive adhesive by admixture with tackifiers, plasticizers or other additives. The term pressure-sensitive adhesive also includes mixtures of different polymers.

In some embodiments, the polymer matrix is a pressure-sensitive adhesive at room temperature and exhibits desirable physical properties, such as good adherence to skin, ability to be peeled or otherwise removed without substantial trauma to the skin, retention of tack with aging, etc. In some embodiments, the polymer matrix has a glass transition temperature ($T_g$), measured using a differential scanning calorimeter, of between about −70° C. and 0° C.

In some embodiments, the compositions in flexible, finite form are "monolithic" or "monolayer" systems, such that the drug-containing polymer matrix layer is the only polymeric layer present other than the backing layer and the release liner, if present. In such embodiments, the polymer matrix functions as both the drug carrier and the means of affixing the system to the skin or mucosa.

Polymer Matrix

In accordance with some embodiments, the compositions described herein comprise a polymer matrix that comprises, consists essentially of, or consists of amphetamine and/or pharmaceutically acceptable salt(s) thereof and at least one acrylic polymer. In this context, the phrase "consists essentially of" means that the polymer matrix is substantially free of other polymer components (e.g., substantially free of polymers other than one or more acrylic polymers) and skin permeation enhancers, although it may include other excipients known to be useful in transdermal compositions (such as tackifiers, plasticizers, crosslinking agents or other excipients known in the art) as long as those other excipients do not degrade the physical and/or pharmacokinetic properties of the compositions to pharmaceutically unacceptable levels.

Amphetamine

Amphetamine (alpha-methylphenethylamine) is a chiral drug. The commercially available oral amphetamine product Adderall® includes several different amphetamine salts, including amphetamine sulfate, amphetamine saccharate, and amphetamine aspartate monohydrate, in an overall ratio of d-amphetamine to l-amphetamine of 3:1. The compositions described herein may be formulated with amphetamine free base or any salt of amphetamine, or any prodrug thereof, or any combinations thereof, and with any isomeric content, and any combinations thereof. In specific embodiments, the compositions comprise d-amphetamine. In further specific embodiments the amphetamine component consists essentially of d-amphetamine (e.g., it contains no more than trace amounts of other amphetamine species). In still further specific embodiments the amphetamine component consists of d-amphetamine. In other specific embodiments, the composition comprises a prodrug of d-amphetamine, such as lisdexamfetamine, in the free base or any salt form, such as lisdexamfetamine dimesylate.

In addition to the salts mentioned above, exemplary suitable pharmaceutically acceptable salts of amphetamine are salts of weak inorganic and organic acids, and quaternary ammonium salts. These include without limitation, salts with acids such as sulfuric, phosphoric, hydrochloric, hydrobromic, hydriodic, sulfamic, citric, lactic, maleic, malic, succinic, tartaric, cinnamic, acetic, benzoic, gluconic, or ascorbic acid, or quaternary ammonium salts with organic esters of sulfuric, hydrohalic, or aromatic sulfonic acids, such as methyl chloride, methyl bromide, ethyl chloride, propyl chloride, butyl chloride, isobutyl chloride, benzylchloride, benzyl bromide, phenethyl bromide, naphthymethyl chloride, dimethyl sulfate, methyl benzenesulfonate, ethyl toluenesulfonate, ethylene chlorohydrin, propylene chlorobydrin, allyl bromide, methylallyl bromide or crotyl bromide esters.

The compositions described herein include a therapeutically effective amount of amphetamine and/or pharmaceutically acceptable salt(s) and/or prodrug(s) thereof. Generally, the amount of amphetamine is from about 1% to about 50%, including from about 5% to about 40%, such as from about 10% to about 20% by weight, based on the total dry weight of the polymer matrix. In specific embodiments, the polymer matrix comprises about 15% by weight amphetamine, based on the total dry weight of the polymer matrix. In other specific embodiments, the polymer matrix comprises about 10% by weight amphetamine, based on the total dry weight of the polymer matrix. In other specific embodiments, the polymer matrix comprises about 20% by weight amphetamine, based on the total dry weight of the polymer matrix.

In accordance with any of the embodiments described herein, the composition may include from about 5 to about 30 mg of amphetamine base or an equivalent amount of a pharmaceutically acceptable salt or prodrug thereof, including about 5, 10, 15, 20, 25, or 30 mg of amphetamine base or equivalent.

Acrylic Polymers

As noted above, in some embodiments the polymer matrix comprises one or more acrylic polymers, such as one or more pressure-sensitive adhesive acrylic polymers. Polymer matrix compositions comprising acrylic polymers are known. In the context of transdermal amphetamine compositions, polymer matrices including a blend of acrylic polymers having different functionalities (e.g., different types and/or amounts of functional groups) that provides a net solubility parameter for the active agent (e.g., amphetamine) have been described. See, e.g., U.S. Patent Application Publication 2003/0170195.

In accordance with specific embodiments, the polymer matrix comprises or consists of one or more non acid-functional acrylic polymers as the polymer component. Non acid-functional acrylic polymers include those formed from acrylic esters copolymerized with other monomers that do not include acid-functional groups. Non acid-functional acrylic polymers include homopolymers, copolymers, terpolymers, etc., of acrylic acids and esters. As used herein, "non acid-functional acrylic polymer" includes polymers that include monomers that have one or more amide groups.

Suitable acrylic polymers can be obtained commercially or by polymerizing or copolymerizing suitable monomers such as acrylic monomers and other polymerizable monomers. Acrylate monomers which can be used include acrylic acid, methacrylic acid, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate. In specific embodiments, the non acid-functional acrylic polymer includes methacrylate (methyl acrylate) monomers and 2-ethylhexyl acrylate monomers. In other specific embodiments the non acid-functional acrylic polymer includes methacrylate (methyl acrylate) monomers, 2-ethylhexyl acrylate monomers, and amide-group containing monomers and optionally butyl acrylate monomers. In other specific embodiments, the non acid-functional acrylic polymer additionally or alternatively includes methyl methacrylate monomers In some embodiments, the non acid-functional acrylic polymer component of the polymer matrix consists of a single non acid-functional acrylic polymer. In other embodiments, the non acid-functional acrylic polymer component of the polymer matrix comprises a blend of a first at non acid-functional acrylic polymer and a second non acid-functional acrylic polymer, and optionally includes additional (e.g., a third or more) non acid-functional acrylic polymers.

Suitable non-acid functional random acrylic polymers which are commercially available include those sold by Henkel North America under the Duro-Tak® brand name such as Duro-Tak® 87-900A, 87-901A, 87-9085, 87-9088, 87-9301A, and by Cytec Industries Inc. under the Gelva® GMS brand name, such as Gelva® GMS 3067, 3071, 3083, 3087 and 3235. Other suitable acrylic polymers are known in the art. See, e.g., the non acid-functional acrylic polymers described in Satas, "Acrylic Adhesives, HANDBOOK OF PRESSURE-SENSITIVE ADHESIVE TECHNOLOGY, 2nd ed., pp. 396-456 (D. Satas, ed.), Van Nostrand Reinhold, N. Y. (1989); "Acrylic and Methacrylic Ester Polymers," POLYMER SCIENCE AND ENGINEERING, Vol. 1, 2nd ed., pp 234-268, John Wiley & Sons, (1984).

When the acrylic polymer component includes more than one non acid-functional acrylic polymer, the polymers can be present in any ratio that results in a product with satisfactory physical and pharmacokinetic properties. For example, the acrylic polymer component can include from 0-100% of a first non acid-functional acrylic polymer and from 100-0% of a second non acid-functional acrylic polymer, based on the total dry weight of the acrylic component, including about 10 to about 90%, about 15-about 85%, about 20 to about 80%, about 25 to about 75%, about 33 to about 66%, and about 50% of the first non acid-functional acrylic polymer, and the balance being the second (or third, etc.) non acid-functional acrylic polymer(s). In specific embodiments, the acrylic polymer component includes about 80% of a first non acid-functional acrylic polymer and about 20% of a second non acid-functional acrylic polymer, based on the total polymer content.

As noted above, in some embodiments, the polymer matrices of the compositions described herein consist essentially of amphetamine or pharmaceutically acceptable salt(s) thereof and at least one non acid-functional acrylic polymer, although such compositions may include other non-polymer components that do not degrade the physical and/or pharmacokinetic properties of the compositions to pharmaceutically unacceptable levels. Generally, for polymer matrices that include amphetamine in an amount from about 1% to about 50%, including from about 5% to about 40%, such as from about 10% to about 35%, or 30%, or 25% by weight, based on the total dry weight of the polymer matrix, the one or more non acid-functional acrylic polymers will constitute from about 99% to about 50%, including from about 95% to about 60%, such as from about 90% to about 65%, or 85% by weight of the polymer matrix, based on the total dry weight of the polymer matrix, with this number being adjusted to account for any excipients. In specific embodiments, the polymer matrix comprises about 85% by weight of one or more non acid-functional acrylic polymers, based on the total dry weight of the polymer matrix.

Backing Layer

The compositions in flexible, finite form comprise a polymer matrix, such as described above, and a backing layer. The backing layer is impermeable to the drug (e.g., impermeable to the amphetamine) and is adjacent one face of the polymer matrix. (By "impermeable" to the drug is meant that no substantial amount of drug loss through the backing layer is observed) The backing layer protects the polymer matrix from the environment and prevents loss of the drug and/or release of other components to the environment during use.

The present inventor surprisingly discovered that the makeup of the backing layer could impact both the drug delivery profile (i.e., the pharmacokinetic profile) and the physical properties of the composition. Therefore, in accordance with some embodiments, the backing layer is selected to achieve a desired drug delivery profile and/or desired physical properties. In specific embodiments, the backing layer is a multi-layer backing layer, such as a multi-layer laminate, that includes a polyurethane film layer and a polyester film layer, with an adhesive disposed between the two layers. In some embodiments, the backing layer consists of a polyester film layer, a polyurethane film layer, and an adhesive disposed between the two layers. In accordance with these embodiments, in the context of the flexible, finite system as a whole, the polyurethane layer of the backing layer is adjacent the polymer matrix. In accordance with some embodiments, the backing layer has a gauge of from about 2 mils to about 5 mils, or thicker. In accordance with some embodiments, the backing layer has a gauge of about 200 (about 2.0 mils) +/−20%.

In accordance with specific embodiments, the polyurethane layer is comprised of a polyether aromatic polyurethane him, such as ST-1882-82 available from Stevens Urethane (Easthampton, Mass.), which has a specific gravity of about 1.14 and a melting point range of about 284 to 320 F (about 140 to 160 C), or ST-1882P-82 available from Stevens Urethane (Easthampton, Mass.) which has a specific gravity of about 1.14 and a melting point range of about 290 to 330 F (about 143 to 166 C).

The present inventor also surprisingly discovered that presence and thickness of the polyurethane layer of the backing layer surprisingly could impact both the drug delivery profile (i.e., the pharmacokinetic profile) and the physical properties of the composition (i.e., acceptable levels of cold flow, including minimal cold flow). Therefore, in accordance with some embodiments, the thickness of the polyurethane layer of the backing layer is selected to achieve a desired drug delivery profile and/or desired physical properties. In some embodiments, the polyurethane film layer has a thickness of from about 1.0 mils to about 2.0 mils. As noted above, in specific embodiments, the polyurethane film layer has a thickness of about 1.5 mils.

In accordance with specific embodiments, the polyester layer is comprised of a polyester film, such as Mylar® 813 available from Dupont Tejin Films (Easthampton, Mass.). In accordance with specific embodiments, the polyester film is a non-metallized film with a moisture vapor transmission rate of about 2.0 g/100 in$^2$/24 hours. In general, the thickness of the polyester layer is selected and controlled to achieve suitable wear and comfort properties, and so the polyester layer may be of any thickness that exhibits acceptable wear and comfort properties. In accordance with some embodiments, the polyester film has a gauge of about 40-60, including a gauge of about 48 or 50 (about 0.5 mils), although films with a gauge of up to 100 or higher (such as up to 300) may be suitable. In specific embodiments, the polyester film layer has a thickness of about 0.5 mils.

The adhesive may be selected to balance competing properties to achieve desired performance under conditions of storage, clinical testing and clinical use. For example, the adhesive may be selected to minimize the risk of separation/delamination of the layers, and/or to achieve a flexible, finite system with the desired flexibility, and/or to exhibit stability under typical storage conditions. In some embodiments, the adhesive is a polyurethane adhesive, such as an isocyanate-terminated polyether urethane or an isocyanate-terminated polyester urethane. In accordance with any embodiments, the adhesive may be a cured adhesive, such as a cured isocyanate-terminated polyether urethane or a cured isocyanate-terminated polyester urethane. For example, the adhesive may be cured by moisture or a curing agent, such as an epoxy curing agent. Additionally or alternatively, in accordance with any embodiments, the adhesive may be a two-component adhesive, such as an adhesive comprising a polyurethane adhesive and a coreactant. In specific embodiments the adhesive is a polyurethane adhesive, such as SW-138 available from Worthen Industries (UPACO Adhesives Division) (Nashua, N.H.). Other suitable adhesives include SW-042 (also from Worthen). In specific embodiments, the adhesive is SW-042 cured with SW-043 (a curative for urethane adhesives, also from Worthen). Such adhesives provide sufficient bonding strength to minimize the risk of separation/delamination upon exposure to water while exhibiting the flexibility required for proper wear and adhesion of the flexible, finite system, and also is stable under typical storage conditions. Other candidate adhesives can be screened for these properties using protocols known in the art, such as those illustrated in the examples. In some embodiments, the adhesive is applied at a thickness of from about 0.1 mils to about 1.0 mils, including about 0.5 mils. In specific embodiments, the adhesive is applied at a thickness of about 0.1 mils The present inventor surprisingly discovered that the choice of backing layer as described herein and the choice of adhesive used in a backing layer as described herein may impact the stability of the composition. For example, transdermal amphetamine compositions made with a backing layer as described herein may exhibit favorable degradation profiles, and may not exhibit the formation of degradants that may be formed with other backing layers. In accordance with some embodiments, the flexible finite systems as described herein are more stable against the formation of degradants as compared to systems prepared with a different backing layer, such as exhibiting the formation of fewer degradant products and/or a lower amount of degradant products. As used herein, the term "degradant" and "degradant products" refers to degradation products of the amphetamine (or pharmaceutically acceptable salt or prodrug thereof), also referred to in the art as "relateds" or "relates." In some embodiments, a flexible finite system as described herein exhibits, after storage at 40° C. for 3.5 months, the formation of at most up to about 1.0% w/w degradants, based on the total weight of amphetamine (or pharmaceutically acceptable salt or prodrug thereof) formulated in the system. In other embodiments, a flexible finite system as described herein exhibits, after storage at 40° C. for 3.5 months, the formation of at most up to about 0.75% w/w degradants, based on the total weight of amphetamine (or pharmaceutically acceptable salt or prodrug thereof) formulated in the system. In other embodiments, a flexible finite system as described herein exhibits, after storage at 40° C. for 3.5 months, the formation of at most up to about 0.5% w/w degradants, based on the total weight of amphetamine (or pharmaceutically acceptable salt or prodrug thereof) formulated in the system. As noted above, specific candidate hacking layers and candidate adhesives therefor can be screened for their impact on stability using protocols known in the art, such as those illustrated in the examples below.

Release Liner

The compositions in flexible, finite form may further comprise a release liner, typically located adjacent the opposite face of the system as the backing layer. When present, the release liner is removed from the system prior to use to expose the polymer matrix layer prior to topical application. Materials suitable for use as release liners are well-known in the art and commercially available, such as polyester release liners, including coated polyester release liners, such as siliconized or fluoro-coated polyester release liners. In specific embodiments, the release liner is a silicone-coated polyester release liner, such as those available from Loparex Inc. (Iowa City, Iowa), including those sold as product D 3.0 CL PET 4000E/000, having a thickness of about 3 mils (+/−10%). In other specific embodiments, the release liner is a fluoropolymer-coated polyester release liner, such as those available from 3M (St. Paul, Minn.), including those sold as Scotchpak™ 9744, having a thickness of about 2.9 mils (+/−0.2 mils).

Methods of Manufacture

The compositions described herein can be prepared by methods known in the art. As one step, the polymer matrices described herein can be prepared by methods known in the art, such as blending (mixing) the at least one non acid-functional acrylic polymer(s) in powder or liquid form with an appropriate amount of drug in the presence of an appropriate solvent, such as a volatile organic solvent, optionally with other excipients. To form a final product, the drug/polymer/solvent mixture may be cast onto a release liner (optionally, at ambient temperature and pressure) followed by evaporation of the volatile solvent(s), for example, at room temperature, slightly elevated temperature, or by a heating/drying step, to form the drug-containing polymer matrix on a release liner. A pre-formed backing layer may be applied to form a final product.

An exemplary general method for preparing a unit final product of a composition as described herein in a flexible, finite form, is as follows:

1. Appropriate amounts of one or more non acid-functional acrylic polymers, solvent(s) and/or co-solvent(s), and optional excipient(s) are combined and thoroughly mixed together in a vessel.

2. The amphetamine is added to the mixture and agitation is carried out until the drug is uniformly mixed therein. (Alternatively, all component can be combined in a mixing vessel such as a drum before any mixing lakes place, and mixing may be effected by tumbling the drum.)

3. The composition is transferred to a coating operation where it is coated onto a release liner at a controlled specified thickness. The coated composition is then passed through an oven in order to drive off all volatile processing solvents.

4. The composition coated on the release liner is then brought into contact with a previously prepared backing layer and wound into rolls.

5. Appropriate size and shape delivery systems are die-cut from the roll material and then pouched.

As set forth above, a backing layer can be prepared by laminating a polyester film layer and a polyurethane film layer, with an adhesive applied between the two layers.

The order of steps, the amount of the ingredients, and the amount and time of agitation or mixing may be important process variables which will depend on the specific polymers, active agents, solvents and/or cosolvents, and optional excipients used in the composition, but these factors can be adjusted by those skilled in the art. The order in which each method step is performed can be changed if needed without detracting from the invention.

In accordance with any of the embodiments of the compositions described herein, the coat weight of the polymer matrix can be, in some embodiments, from about 3 mg/cm$^2$ to about 10 mg/cm$^2$, based on the active surface area of the polymer matrix. Exemplary coat weights include about 3 mg/cm$^2$, about 4 mg/cm$^2$, about 5 mg/cm$^2$, about 5.5 mg/cm$^2$, about 6 mg/cm$^2$, about 6.5 mg/cm$^2$, about 7 mg/cm$^2$, about 7.5 mg/cm$^2$, about 8 mg/cm$^2$, about 8.5 mg/cm$^2$, about 9 mg/cm$^2$, about 9.5 mg/cm$^2$, and about 10 mg/cm$^2$. In specific embodiments the coat weight of the polymer matrix is about 6.0 to about 8.0 mg/cm$^2$, including about 7.0 mg/cm$^2$, based on the active surface area of the of the polymer matrix.

In accordance with any of the embodiments of the compositions described herein, the amphetamine can be present, in some embodiments, in an amount from about 0.5 mg/cm$^2$ to about 3 mg/cm$^2$, based on the active surface area of the of the polymer matrix, such as about 1 mg/cm$^2$, including about 1.05 mg/cm$^2$, based on the active surface area of the of the polymer matrix. Other exemplary amounts include about 0.75 mg/cm$^2$, 0.8 mg/cm$^2$, 0.9 mg/cm$^2$, 1.0 mg/cm$^2$, 1.05 mg/cm$^2$, 1.1 mg/cm$^2$, 1.2 mg/cm$^2$, and 1.25 mg/cm$^2$, 1.5 mg/cm$^2$, 2.0 mg/cm$^2$. 2.5 mg/cm$^2$, and 3.0 mg/cm$^2$.

In accordance with any of the embodiments of compositions described herein, the size of the final product (e.g., the composition in the form of a the flexible, final system) may be, in some embodiments, in the range of from about 2 cm$^2$ to about 60 cm$^2$, including from about 5 cm$^2$ to about 30 cm$^2$, including about 4.75 cm$^2$, 5 cm$^2$, 10 cm$^2$, 15 cm$^2$, 20 cm$^2$, 25 cm$^2$, and 30 cm$^2$. In specific embodiments, the final product includes an amount of amphetamine of about 1.05 mg/cm$^2$, such that, for example, a 5 cm$^2$ flexible, finite system includes about 5.25 mg amphetamine, and flexible, finite systems having a size of 10 cm$^2$, 15 cm$^2$, 20 cm$^2$, 25 cm$^2$, and 30 cm$^2$ have proportionate amounts of amphetamine.

Methods of Use

The compositions described herein are useful in methods for the transdermal delivery of amphetamine, including in methods for treating attention deficit disorder, attention deficit hyperactivity disorder, and/or narcolepsy. In such embodiments, a composition comprising a therapeutically effective amount of amphetamine as described herein is topically applied to a subject in need thereof.

The compositions described herein achieve a transdermal flux of amphetamine (and/or one or more pharmaceutically acceptable salt(s) thereof) that is sufficient to have a therapeutic effect. As used herein. "flux" (also called "permeation rate") is defined as the absorption of a drug through skin or mucosal tissue, and is described by Fick's first law of diffusion:

$$J=-D(dCm/dx)$$

where J is the flux in g/cm$^2$/sec, D is the diffusion coefficient of the drug through the skin or mucosa in cm$^2$/sec and dCm/dx is the concentration gradient of the drug across the skin or mucosa.

In some embodiments, the compositions achieve transdermal delivery of amphetamine over a period of time of about 8 to 10 hours, including a period of time of about 9 hours, although the composition may be applied for a shorter or longer period of time. In some embodiments, the compositions achieve transdermal delivery of therapeutically effective amounts of amphetamine over a period of time of about 8 to 10 hours, including a period of time of about 9 hours, although the composition may be applied on the application site for a shorter or longer period of time.

In accordance with some embodiments, the compositions described herein achieve delivery of at least about 80% of the amphetamine within a period of time of about 8 to 10 hours, including at least about 90%, or greater. These embodiments offer advantages, such as the ability to leave the compositions in place without resulting in the delivery of additional amphetamine, which may not be desired once the intended dose has been delivered.

In accordance with another aspect, there are provided transdermal compositions in flexible, finite form that exhibit a short onset period and a long duration of therapeutic effect. The two commercially available oral products, the Adderall® product and the Vyvanse® product, exhibit one or the other effect. For example. Adderall® has a rapid onset of about 30 minutes, but a duration of therapeutic effect or only 6-8 hours. On the other hand, Vyvanse® (an oral pharmaceutical product comprising capsule of lisdexamfetamine dimesylate, a prodrug of d-amphetamine), has a longer duration of therapeutic effect, but an onset period of about 2 hours. In contrast, provided herein are transdermal compositions in flexible finite form that achieve a drug delivery profile that exhibits both rapid onset and an extended duration of therapeutic effect, and so achieves desirable pharmacokinetic effects that have not heretofore been possible.

Thus, in accordance with specific embodiments, provided herein are transdermal compositions in flexible finite form that exhibit an onset period of about 30 minutes to about 90 minutes, or about 45 to about 60 minutes, including about 30 minutes, about 45 minutes, about 60 minutes, and about 75 minutes. As used herein, "onset period" refers to the time it takes to achieve circulating blood (plasma) levels of amphetamine after application of the composition, such as circulating blood (plasma) levels of at least about 2 ng/ml, including about 2 ng/ml to about 5 ng/ml, or about 3 ng/ml to about 4 ng/ml. Also provided herein are transdermal compositions in flexible finite form that, additionally or alternatively, exhibit a duration of therapeutic effect of at least about 12 hours, including about 12 to about 16 hours, including about 14 hours, from the time of application of the composition, when it is removed at about 9 hours after application. Also provided herein are transdermal compositions in flexible finite form that, additionally or alternatively, exhibit a drug depletion such that at least about 85% to about 93% of the drug formulated in the compositions, including about 90%, is delivered or depleted from the composition at about 8-10 hours after application, such as at about 9 hours after application. (The foregoing parameters are described with reference to a 9 hour application period because currently approved protocols for the administration of transdermal methylphenidate patches call for their removal by about 9 hours after application. This detail is not limiting of the scope of the invention or the pharmacokinetic properties of the compositions described herein.)

In accordance with some embodiments, the compositions described herein above in more detail (e.g., comprising a polymer matrix and backing as described herein above and illustrated in the examples) exhibit one or more of (a) an onset period of about 30 minutes to about 90 minutes, or about 45 to about 60 minutes, including about 30 minutes, about 45 minutes, about 60 minutes, and about 75 minutes; (b) a duration of therapeutic effect of at least about 12 hours, including about 12 to about 16 hours, including about 14 hours, from the time of application of the composition, when it is removed at about 9 hours after application; and/or (c) a drug depletion such that at least about 85% to about 93% of the drug formulated in the compositions, including about 90%, is delivered or depleted from the composition at about 8-10 hours after application, such as at about 9 hours after application. However, this aspect of the invention is not limited to these specific embodiments.

The following specific examples are included as illustrative of the compositions described herein. These example are in no way intended to limit the scope of the invention. Other aspects of the invention will be apparent to those skilled in the art to which the invention pertains.

EXAMPLE 1A

A polymer matrix composition is prepared with the following components, based on the dry weight of the polymer matrix:
67.5% by weight of a pressure-sensitive acrylic polymer comprised of 50% methacrylate monomers (MA) and 50% 2-ethylhexyl acrylate monomers (2-EHA)
17.5% by weight of a pressure-sensitive acrylic polymer comprised of MA monomers, 2-EHA monomers, butyl acrylate monomers, and amide group-containing monomers
15% by weight d-amphetamine The polymer matrix is applied to a release liner and dried.

A laminated backing layer is prepared by laminating a 1.5 mils thick polyurethane film layer (ST-1882-82, Stevens Urethane) to a 0.5 mils thick polyester film layer (Mylar® 813, Dupont Teijin Film) with adhesive SW-138 (Worthen Industries), applied at a thickness of about 0.1 mils.

The backing layer is applied to the polymer matrix to form a flexible, finite system with the polyurethane film layer adjacent the polymer matrix layer.

EXAMPLE 1B

A polymer matrix composition is prepared with the following components, based on the dry weight of the polymer matrix:
67.5% by weight of a pressure-sensitive acrylic polymer comprised of 50% methacrylate monomers (MA) and 50% 2-ethylhexyl acrylate monomers (2-EHA)
17.5% by weight of a pressure-sensitive acrylic polymer comprised of MA monomers, 2-EHA monomers, butyl acrylate monomers, and amide group-containing monomers
15% by weight d-amphetamine The polymer matrix is applied to a release liner and dried.

A laminated backing layer is prepared by laminating a 1.5 mils thick polyurethane film layer (ST-1882-82, Stevens Urethane) to a 0.5 mils thick polyester film layer (Mylar® 813. Dupont Teijin Film) with adhesive SW-042 cured with curing agent SW-043 (Worthen Industries), applied at a thickness of about 0.1 mils.

The backing layer is applied to the polymer matrix to form a flexible, finite system with the polyurethane film layer adjacent the polymer matrix layer.

EXAMPLE 2

The following example evaluates the propensity of a backing layer as described herein to undergo separation/delamination when exposed to water.

The flexible, finite systems prepared as described in Example 1B is immersed in water and does not exhibit any delamination after 24 hours. In contrast, flexible, finite systems prepared with backing layers comprised of a polyurethane film layer and a polyester film layer, with different adhesives used between the polyurethane film layer and the polyester film layer (ADCOTE™ 503E/F or ADCOTE™ 577/577B, both from Dow), exhibited partial delamination after 15 minutes and the layers of the laminated backing layer were fully delaminated after 45 minutes.

EXAMPLE 3

The following example evaluates the stability of a flexible, finite system as described herein with regard to the production of degradation products.

Flexible, finite systems prepared as described in Example 1B are stored for 3.5 months at 40° C. and exhibit good stability, include good stability with regard to amphetamine content and low production of degradation products. In contrast, flexible, finite systems prepared with hacking layers comprised of a polyurethane film layer and a polyester film layer, with different adhesives used between the polyurethane film layer and the polyester film layer exhibited greater formation of degradation products, as shown below.

| Backing | Amphetamine Content. (mg/unit) | Amphetmaine Content (mg/g) | Number of Degradants Detected | Amount of Degradants (% w/w) |
|---|---|---|---|---|
| Bemis 3071 PU/PET | 11.2 | 131.9 | 5 | 0.93 |
| Graphic Packaging AdCode 102E/F PU/PET | 10.3 | 132.9 | 7 | 1.69 |
| Example 1B | 13.5 | 168.1 | 2 | 0.38 |

EXAMPLE 4

Figure 1B:
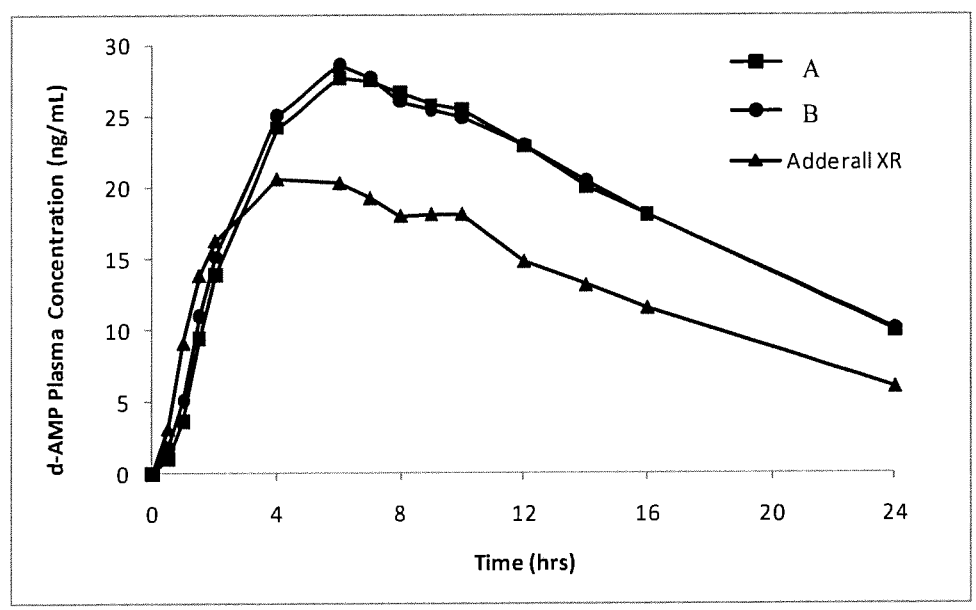
FIG. 1B is an expanded view of the 0-24 hour data of FIG. 1A.

A Phase 1 clinical study was conducted to assess pharmacokinetics, safety and tolerability of the system described in Example 1B in children with ADHD, using the oral Adderall® XR product as a comparison. The study design was an open-label, single-center, randomized, single-dose, 3-way crossover study with three periods, with a washout period of at least 4 days in between treatments.
Treatment A: 8.4 mg/8.0 cm$^2$ system applied for 9 hours
Treatment B: 8.4 mg/8.0 cm$^2$ system applied for 12 hours
Treatment C: one Adderall® XR 10 mg capsule Blood samples were drawn periodically over 48 hours and analyzed for d- and l-amphetamine. Results (d-amphetamine conc. (mg/ml) vs. time) are shown in FIGS. 1A and 1B (expanded view of 0-24 hours). As seen in the figures, the systems of Example 1 exhibit rapid onset and sustained drug delivery.

| Onset | | |
|---|---|---|
| Treatment | Time (hr) | d-amphetamine (ng/ml) |
| A | 0.5 | 0.94 |
| B | | 1.65 |
| C | | 3.17 |
| A | 1.0 | 3.59 |
| B | | 4.77 |
| C | | 9.11 |
| A | 1.5 | 9.45 |
| B | | 10.21 |
| C | | 13.84 |
| A | 2.0 | 13.83 |
| B | | 14.11 |
| C | | 16.27 |

| Treatment | Duration Time (hr) | d-amphetamine (ng/ml) |
|---|---|---|
| A | 14 | 20.02 |
| B |  | 20.46 |
| C |  | 13.16 |
| A | 16 | 18.04 |
| B |  | 18.08 |
| C |  | 11.56 |
| A | 24 | 9.88 |
| B |  | 10.09 |
| C |  | 6.04 |
| A | 36 | <0.5 |
| B |  | <0.5 |
| C |  | <0.5 |

For Treatment A, the systems were about 89% depleted after 9 hours, and delivered an apparent dose of about 6.9 mg after 9 hours. For Treatment B, the systems were about 93% depleted after 12 hours, and delivered an apparent dose of about 7.1 mg after 12 hours. The relative bioavailability of d-amphetamine over 24 hours was calculated as follows:
Treatment A/Treatment C (Oral)=96%
Treatment B/Treatment C (Oral)=92%
Treatment A/Treatment B=106%

The average apparent relative transdermal vs. oral bioavailability across the study was about 90-100%. Both transdermal treatments achieved total amphetamine concentration/time profiles similar to Adderall® XR, although Adderall® XR had a shorter onset period (about 0.1 hours as compared to about 0.5 hours) and the transdermal treatments exhibited higher plasma concentrations after about 6 hours as compared to Adderall® XR.

The wear properties also were assessed. For Treatment A, 88% of the systems exhibited good adhesion (essentially no lift-off from the skin) for the 9 hour application period. For Treatment B, 94% of the systems exhibited good adhesion (essentially no lift-off from the skin) for the 12 hour application period. For Treatment A, 41% left no adhesive residue and 47% left a light adhesive residue (some were not assessed). For Treatment B, 78% left no adhesive residue and 17% left a light adhesive residue (some were not assessed).

Overall, the transdermal systems were safe and tolerable with a safety profile similar to that of the Adderall® XR reference product.

EXAMPLE 5

A clinical study was conducted to assess pharmacokinetics of different doses of systems formulated as described in Example 1 in children with ADHD. The study design was an open-label, single-center, randomized, single-dose, 3-way crossover study with three periods, with a washout period of 7 days in between treatments.

Figure 2:
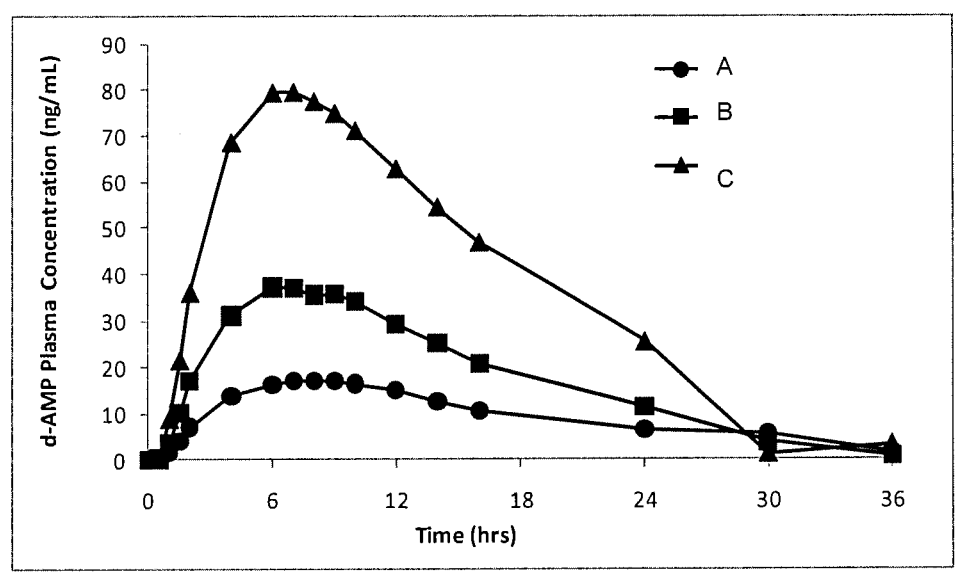
FIG. 2 shows plasma levels of d-amphetamine (mg/ml) over 36 hours after Treatment A (♦), Treatment B (■) or Treatment C (▲) of Example 5 below.

Treatment A: 5 mg/4.76 cm$^2$ system applied for 9 hours
Treatment B: 10 mg/9.52 cm$^2$ system applied for 9 hours
Treatment C: 20 mg/19.05 cm$^2$ system applied for 9 hours Blood samples were drawn periodically over 36 hours and analyzed for d- and l-amphetamine. Results (d-amphetamine conc. (mg/ml) vs. time) are shown in FIG. 2. As seen in the figure, the systems of Example 1 exhibit rapid onset and sustained drug delivery, with a dose-dependent plasma concentration profile.

For Treatment A, the systems were about 89% depleted after 9 hours, and delivered an apparent dose of about 4.42 mg after 9 hours, with a mean onset time of about 0.6 hours, a mean Cmax of about 18.8 ng/ml, a mean Tmax of 9.00 hours, and a mean AUC(24 hours) of 282.56 ng*hr/ml. For Treatment B, the systems were about 91% depleted after 9 hours, and delivered an apparent dose of about 9.01 mg after 9 hours, with a mean onset time of about 0.4 hours, mean Cmax of about 39.7 ng/ml, mean Tmax of 7.2 hours, and mean AUC(24 hours) of 582.17 ng*hr/ml. For Treatment C, the systems were about 90% depleted after 9 hours, and delivered an apparent dose of about 18.0 mg after 9 hours, with a mean onset time of about 0.4 hours, mean Cmax of about 85.4 ng/ml, mean Tmax of 6.9 hours, and mean AUC(24 hours) of 1260.60 ng*hr/ml.

Overall, the transdermal systems exhibited linear pharmacokinetic profiles over doses ranging from 5 to 20 mg.

What is claimed is:

1. A method of making a composition for the transdermal delivery of amphetamine in the form of a flexible finite system for topical application, comprising combining (i) a polymer matrix comprising amphetamine or a pharmaceutically acceptable salt or prodrug thereof and (ii) a backing layer comprising (a) a polyurethane film layer and (b) a polyester film layer, wherein a polyurethane adhesive is disposed between the polyurethane film layer and the polyester film layer, wherein the polyurethane film layer of the backing layer is adjacent the polymer matrix.

2. The method of claim 1, wherein the polyurethane film layer is comprised of a polyether aromatic polyurethane polymer.

3. The method of claim 1, wherein the polyurethane film layer has a thickness of about 1.5 mils.

4. The method of claim 1, wherein the polyester film layer has a thickness of from about 0.4 mils to 0.6 mils.

5. The method of claim 1, wherein the amphetamine is d-amphetamine free base.

6. The method of claim 1, wherein the polymer matrix comprises at least one acrylic polymer.

7. The method of claim 1, wherein the polymer matrix comprises at least one non acid-functional acrylic polymer.

8. The method of claim 7, wherein at least one non acid-functional acrylic polymer includes methacrylate and 2-ethylhexyl acrylate monomers and, optionally, methyl methacrylate monomers.

9. The method of claim 7, wherein at least one non acid-functional acrylic polymer includes methacrylate, 2-ethylhexyl acrylate, and amide group-containing monomers, and, optionally, methyl methacrylate monomers.

10. The method of claim 1, wherein the polymer matrix comprises about 10-20% by weight amphetamine or a pharmaceutically acceptable salt or prodrug thereof.

11. The method of claim 1, wherein the polymer matrix comprises (a) first non acid-functional acrylic polymer that includes 50% methacrylate monomers and 50% 2-ethylhexyl acrylate monomers, based on the weight of the first acrylic polymer; (b) a second non acid-functional acrylic polymer that includes methacrylate monomers, 2-ethylhexyl acrylate monomers, and amide group-containing monomers, and (c) about 10-20% by weight amphetamine or a pharmaceutically acceptable salt or prodrug thereof.

12. The method of claim 11, wherein the polymer matrix consists of 67.5% by weight of said first non acid-functional acrylic polymer, 17.5% by weight of said second non acid-functional acrylic polymer, and 15% by weight amphetamine, based on the total dry weight of the polymer matrix.

13. The method of claim 1, wherein the polymer matrix has a coat weight of about 6-8 mg/cm$^2$, based on the active surface area of the polymer matrix.

14. The method of claim 1, wherein the composition comprises about 1 mg/cm$^2$ amphetamine.

15. The method of claim 1, wherein the flexible, finite system has a size of from about 2 cm$^2$ to about 60 cm$^2$.

16. The method of claim 1, further comprising providing a release liner on a face of the polymer matrix not adjacent the backing layer.

17. The method of claim 1, wherein the composition delivers amphetamine over a period of time of about 8-10 hours.

18. The method of claim 1, wherein the composition exhibits an onset period of from about 30 minutes to about 90 minutes.

19. The method of claim 1, wherein the composition exhibits a duration of therapeutic effect of at least about 12 hours from the time of application of the composition, when it is removed at about 9 hours after application.

20. The method of claim 1, wherein the composition exhibits a drug depletion of at least about 85% to about 93% at about 8 to 10 hours after application.

* * * * *